United States Patent
Joung et al.

(10) Patent No.: US 7,312,456 B2
(45) Date of Patent: Dec. 25, 2007

(54) STATIONARY MULTI-PINHOLE CARDIO VASCULAR SPECT SYSTEM

(75) Inventors: Jinhun Joung, Algunquin, IL (US); John C. Engdahl, Peoria, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 35 days.

(21) Appl. No.: 11/237,426

(22) Filed: Sep. 28, 2005

(65) Prior Publication Data

US 2006/0065840 A1 Mar. 30, 2006

Related U.S. Application Data

(60) Provisional application No. 60/613,898, filed on Sep. 28, 2004.

(51) Int. Cl.
*G01T 1/166* (2006.01)
(52) U.S. Cl. .......................... 250/363.05; 250/363.04; 250/363.08; 250/363.1

(58) Field of Classification Search ........... 250/363.05, 250/363.08, 363.04, 363.1
See application file for complete search history.

(56) References Cited

U.S. PATENT DOCUMENTS 6,242,743 B1 * 6/2001 DeVito et al. ......... 250/363.05
2004/0149923 A1 * 8/2004 Beekman .................... 250/393

OTHER PUBLICATIONS

Rowe, R.K. et al., "A Stationary Hemispherical SPECT Imager for Three-Dimensional Brain Imaging," The Journal of Nuclear Medicine, vol. 34, No. 3 (Mar. 1993) pp. 474-480.*

* cited by examiner

*Primary Examiner*—Constantine Hannaher

(57) ABSTRACT

A dynamic Single Photon Emission Computed Tomography (SPECT) system utilizes an array of modular detectors structured in a dome shape and being independently tiltable in polar or azimuth angle. The system can be used to image cardio-vascular studies as well as other quantitative studies and 3D imaging studies, without requiring movement or motion of the detectors.

15 Claims, 4 Drawing Sheets

STATIONARY MULTI-PINHOLE CARDIO VASCULAR SPECT SYSTEM

CROSS-REFERENCE TO RELATED APPLICATION AND CLAIM FOR PRIORITY

This application claims priority under 35 U.S.C. § 119(e) from copending provisional application Ser. No. 60/613,898 filed Sep. 28, 2004.

BACKGROUND OF THE INVENTION

1. Field of the Invention

The present invention generally relates to nuclear imaging. In particular, the present invention relates to systems and methods for pinhole collimator imaging.

2. Description of the Background Art

The ability of nuclear medicine modalities to provide physiologic functions in vivo, the metabolism of several substrates, and the binding potential of particular receptors of the cardiovascular system has brought incremental value to nuclear cardiology and has broadened the clinical relevancy of the modality.

Many treatment algorithms in cardiology use the left ventricle ejection fraction as an initial measure in clinical decision making. Noninvasive myocardium perfusion imaging should guide the physician in planning the appropriate management of patients with known or suspected coronary artery disease. In addition, dynamic (quantitative) cardiac imaging provides quantification in particular physiologic processes and biochemical pathways of interest based on kinetic modeling.

However, despite a relatively long history of cardiac Single Photon Emission Computed Tomography (hereinafter referred to as SPECT) imaging, greater radiotracer availability and longer-lived isotopes, dynamic imaging is generally regarded as the exclusive domain of positron emission tomography (PET), and only limited attempts have been made to extract quantitative physiologic parameters using SPECT. The main limitation of dynamic SPECT is its inferior detection efficiency and spatial resolution as compared with PET.

Other challenging aspects of imaging cardiovascular SPECT are the anatomical location of the heart, bulky detectors and the movement of the myocardium.

The heart is located in the middle of the chest behind the breastbone, between the lungs, and rests in a moistened chamber called the pericardial cavity which is surrounded by the ribcage. Further, a layer of muscle lies below the heart. As a result, the heart is well protected, but difficult to image. In addition, conventional gamma cameras are heavy and bulky because they have a very large single crystal, typically 40×60 $cm^2$, coupled to a heavy collimator so that it has limited access to the body contour and view angle.

The most common way to address the movement problem in existing devices is a procedure called MUGA (multiple gated acquisition) that involves gating of the image acquisition with R-wave signals from an EKG and generating time-slice images per cardiac cycle. To avoid motion blur, a high count rate capability is typically recommended.

Existing SPECT imaging allows for multiple 2-D images to be taken from different angles then recreated using a SPECT computer program to produce a 3-D image.

Further, existing SPECT imaging creates an image utilizing a scintillator. A scintillator is a material that has the ability to absorb a photon and convert that energy into light. Scintillators are used to detect the energy given off by a radioactive isotope. Existing scintillators should be able to convert much of the incident energy to light. Existing scintillators can be either organic or inorganic with each having their own benefits depending on the intended use.

Additionally, existing SPECT imaging also uses collimators to limit the direction of impinging photons as they approach the scintillator. Generally, existing collimators are made out of lead, tungsten, or copper-beryllium. There are two principal types of collimators used in medical imaging. The pin-hole collimator is primarily used in studying very localized objects such as a gland or other organ. It consists of a dense material with a single small hole drilled in the middle. Pin-hole collimators offer the benefit of high magnification of a single object, but lose resolution and sensitivity as the field of view gets wider. On the other hand, a parallel-hole collimator consists of a large number of holes drilled or etched into the material that accept photons only moving perpendicular to the scintillator.

SUMMARY OF THE INVENTION

The present invention overcomes the existing problems in the prior art by placing an emphasis on system design to address the challenging aspects of a cardio-vascular SPECT system. The system design enables dynamic imaging without detector motion and provides high spatial and temporal resolution as well.

Moreover, the present invention can allow for additional projections to be sampled with an optional spin motion and high detection efficiency which allows for quantitative SPECT imaging.

The present invention also allows each detector module to be tilted to secure the best view angle. Further, modular detectors enable a high count rate capability. Also, the present invention allows for high maneuverability and approachability with modular detectors.

Further, the present invention's use of multi pinhole collimation makes it feasible to design a system in such a way that it offers 3-D reconstruction of images with relatively few detectors and without motion. Also, due to simultaneous acquisition through the multi pinhole apertures, the detection efficiency of the system reaches enough range to allow for dynamic (quantitative) imaging.

The present invention also eliminates the need for projection multiplexing and minimizes parallax error by restricting gamma rays that are impinging with a wide angle through the use of lead septa between adjoining pinholes.

BRIEF DESCRIPTION OF THE DRAWINGS

The invention will become more clearly understood from the following detailed description in connection with the accompanying drawings, in which.

in case of 5 cm distance, i.e., 0.5 magnification factor and 13 degree acceptance angle, the system spatial resolution is about 5 mm @ 10 cm depth and the sensitivity is 2.5 cps/uci/module).

DETAILED DESCRIPTION OF THE PREFERRED EMBODIMENTS

Figure 1A:
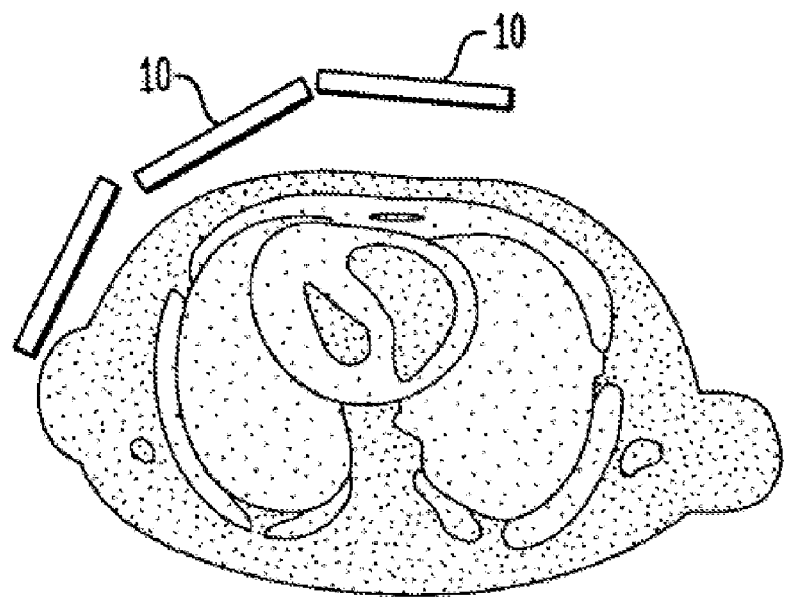
FIG. 1A is a cross sectional view of a feature of the present invention wherein detectors are tilted such that they secure the best viewing angle to the object.
Figure 1B:
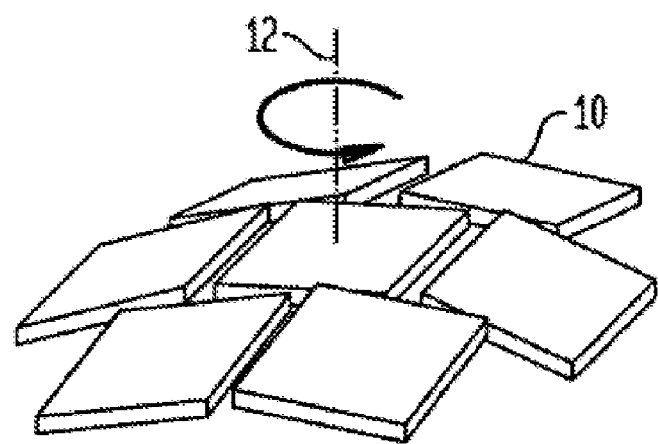
FIG. 1B is a three dimensional view of a feature of the present invention wherein the imaging system can optionally spin (e.g. to increase projection samples)

Referring to FIGS. 1(A)-1(B), according to one preferred embodiment of the invention, a SPECT imaging system includes a number of modular detectors 10 arrayed together to have an overall curvature in the shape of a section of a dome, as best seen in FIG. 1(B). The modular detectors 10 can vary in size and number depending on the system integration and imaging specification prerequisites. Further, in some embodiments the size of the detector is chosen in a manner which provides high maneuverability and approachability to the body while maintaining the necessary field of view. In addition, in some preferred embodiments the modules can be tilted to any polar and/or azimuth angle, e.g., to secure the best angle view to the heart (FIG. 1(A)). In a particular preferred embodiment, the detector system is allowed to spin about an axis 12 through the heart to acquire additional angular projections (FIG. 1(B)).

Figure 2A:
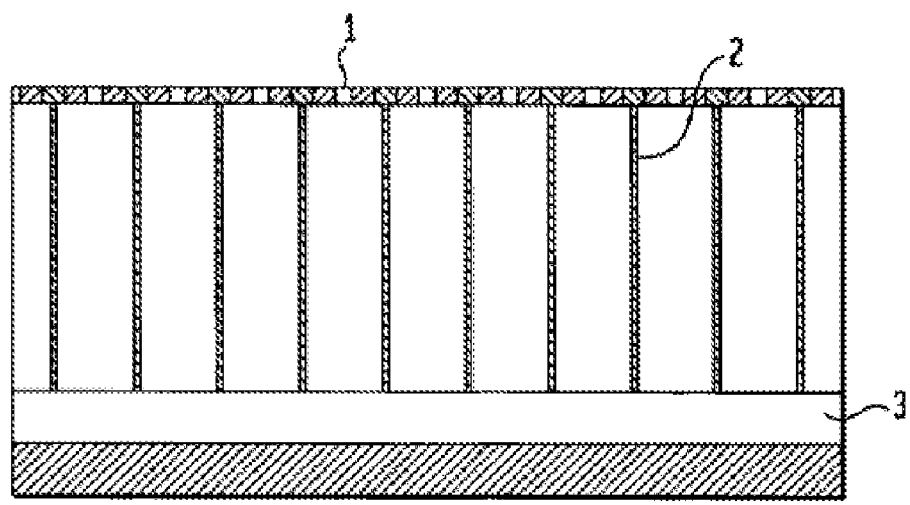
FIG. 2A is a cross-sectional view of a multi-pinhole detector module wherein the length of the lead septa determines the magnification factor and acceptance angle.
Figure 2B:
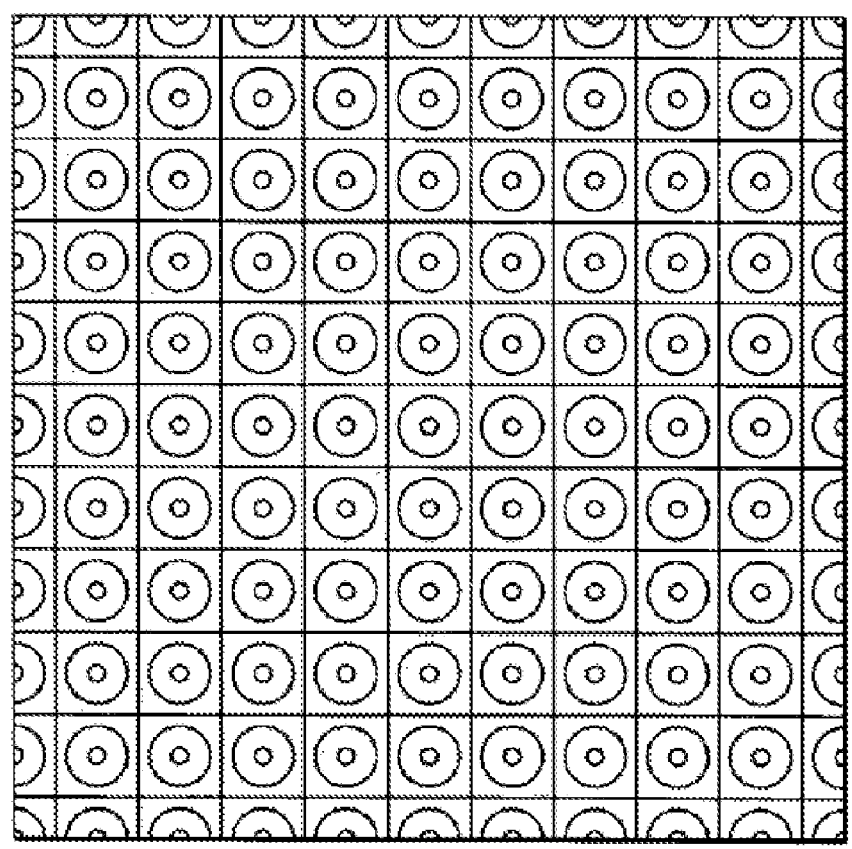
FIG. 2B is a top view of a multi-pinhole detector module.

As shown in FIGS. 2(A) and 2(B), according to one embodiment of the invention, multi-pinhole collimation is used in conjunction with the modular detector array. Lead septa 2 are placed in between tungsten pinhole apertures 1, which are located above a scintillator 3. The septa 2 prevent gamma photon projections from overlapping with each other, and thus eliminate the need for projection multiplexing, which is required in most conventional multi-pinhole and coded aperture systems. The use of the septa 2 also minimizes parallax error by restricting out wide-angle impinging gamma rays.

The use of multi-pinhole collimation allows reconstruction of 3D images with relatively few detectors and without movement of the detectors. As a result of simultaneous acquisition through the multiple pinhole apertures, system detection efficiency is increased to a range that is sufficient for dynamic (i.e., quantitative) imaging.

Figure 3A:
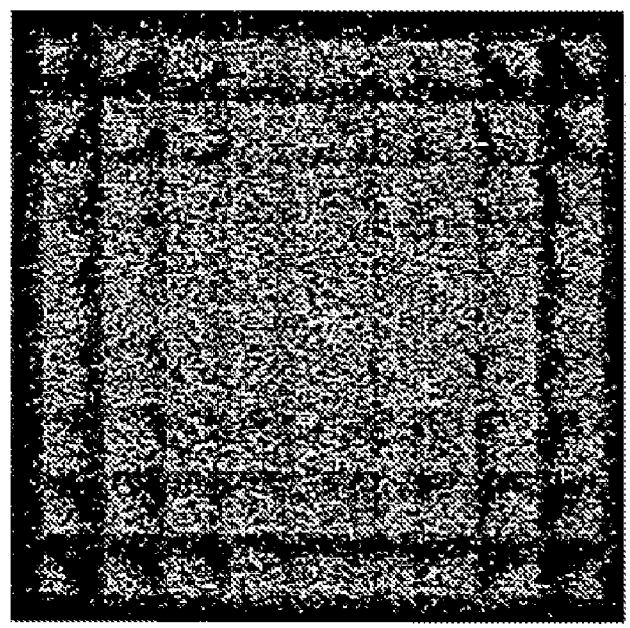
FIG. 3A is a Monte Carlo simulation wherein projection images of a spherical source (10 cm diameter) placed at 10 cm above from the multi-pinhole plate (2.5 cps/uci)
Figure 3B:
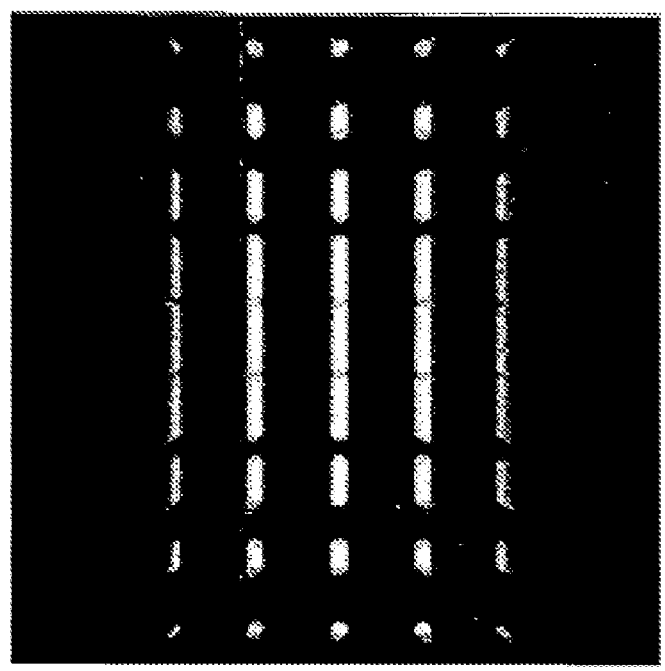
FIG. 3B is a Monte Carlo simulation wherein projection images of a spherical source wherein a line source (5 cm long) placed at 10 cm above, parallel to y-axis. (5.2 mm FWHM)

FIGS. 3(A) and 3(B) show Monte Carlo simulations of projections obtained from a spherical source and line source, respectively. These simulations were conducted in order to assess the sensitivity and spatial resolution of the system according to the invention. In the simulation, the detector module was of size 10×10 $cm^2$ with 81 pinholes (each of 2 mm diameter), and a magnification factor of 0.5. The spherical source was 10 cm in diameter with a uniform activity concentration, and the line source was 5 cm in length and 0.2 mm in diameter. 20 million counts were acquired for each projection.

Figure 4:
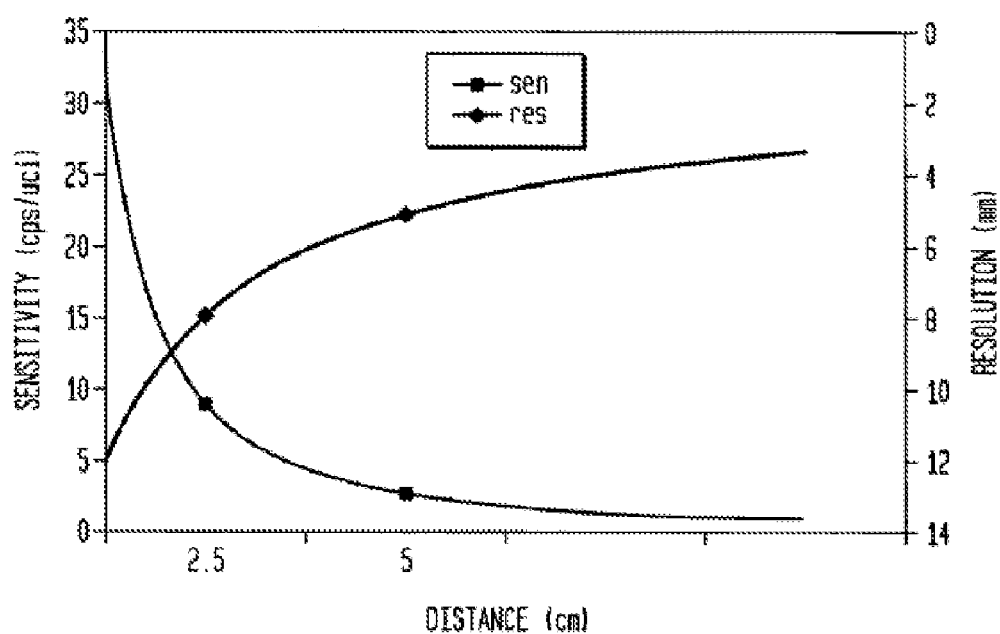
FIG. 4 is a chart illustrating sensitivity and resolution trade-off as a function of detector-pinhole plate distance (e.g.

FIG. 4 shows the trade-off between sensitivity and resolution as a function of the distance between the scintillator and the multi-pinhole plate, which determines the magnification factor and acceptance angle. In the example using a 2 mm pinhole diameter and a magnification factor of 0.5, the expected system spatial resolution is approximately 5 mm FWHM at 10 cm depth of the object from the surface of the collimator, and the sensitivity is approximately 2.53 cps/μci/ module. Thus, a system having 10 detector modules would have a sensitivity of about 25 cps/μci, which is about 3 times more sensitive than a typical dual head SPECT system.

In a preferred embodiment the present invention is used as a cardio-vascular imager. However, the versatility of the system makes it possible to extend applications to other objects such as joints, the head, breast, and/or various internal organs.

The present invention provides many benefits and advantages over the prior art, including: 3D SPECT imaging without requiring detector movement; sampling of additional projections by using optional axial-spin motion; quantitative SPECT imaging enabled by higher detection efficiency; obtainment of best view angle by ability to tilt each detector module individually; and high maneuverability and approachability of objects to be imaged.

The invention having been described, it will be apparent to those skilled in the art that the same may be varied in many ways without departing from the spirit and scope of the invention. Any and all such modifications are intended to be included within the scope of the following claims.

What is claimed is:

1. A single photon emission computed tomography (SPECT) detection system, comprising a plurality of modular detectors arrayed together to have an overall curvature in the shape of a section of a dome, and a multi-pinhole collimator coupled to each of said plurality of modular detectors.

2. The SPECT system of claim 1, wherein said array of modular detectors includes the ability for each detector to be tilted to any polar angle.

3. The SPECT system of claim 1, wherein said array of modular detectors includes the ability for each detector to be tilted to any azimuth angle.

4. The SPECT system of claim 1, wherein said array of modular detectors includes the ability for each detector to be tilted to any polar or azimuth angle.

5. The SPECT system of claim 1, wherein the size of said modular detectors is selectable so as to provide high maneuverability.

6. The SPECT system of claim 1, wherein the size of said modular detectors is selectable to allow for approachability to the body while maintaining a necessary field of view.

7. The SPECT system of claim 1, wherein the detector array includes the ability to spin around the object to be imaged about an axis in a direction of said object, so as to obtain additional projection angle samples.

8. The SPECT system of claim 1, wherein said object is a heart.

9. The SPECT system of claim 1, wherein said object is an internal organ.

10. The SPECT system of claim 1, wherein said object is an anatomical joint.

11. The SPECT system of claim 1, wherein said object is the head.

12. The SPECT system of claim 1, wherein said object is a breast.

13. The SPECT system of claim 1, wherein said object is a part of the human body.

14. The SPECT system of claim 1, wherein said multi-pinhole collimator comprises lead septa placed between adjoining pinhole apertures.

15. A method of SPECT imaging, comprising:
providing a detector system having an array of modular detectors arranged to have an overall curvature in the shape of a section of a dome; and
spinning said detector array around an object to be imaged about an axis in a direction of said object, so as to obtain additional projection angle samples.

* * * * *